United States Patent [19]

Berger

[11] Patent Number: 4,651,735

[45] Date of Patent: Mar. 24, 1987

[54] CURETTE BLADE HOLDER

[75] Inventor: Jacob E. Berger, Amherst, N.Y.

[73] Assignee: Obex Industries, Inc., Amherst, N.Y.

[21] Appl. No.: 749,551

[22] Filed: Jun. 27, 1985

[51] Int. Cl.⁴ ............................................. A61B 17/22
[52] U.S. Cl. ........................................ 128/304; 30/49
[58] Field of Search .................. 128/304, 305, 305.5, 128/757, 354; 30/49, 75, 51, 331, 330, 53; 132/76.4

[56] References Cited

U.S. PATENT DOCUMENTS

| | | | |
|---|---|---|---|
| 1,940,563 | 12/1933 | Porter et al. | 30/75 |
| 2,089,486 | 8/1937 | Kuhn | 30/49 |
| 2,613,438 | 10/1952 | Robinson | 30/331 |
| 2,657,460 | 11/1953 | Cerino et al. | 30/49 |
| 2,662,281 | 12/1953 | Cerino | 30/58 |
| 3,077,034 | 2/1963 | Stineman | 30/331 |
| 3,154,852 | 11/1964 | Westlake, Jr. | 30/51 |
| 3,353,531 | 11/1967 | Armao | 128/305 |
| 3,861,034 | 1/1975 | Cerino | 30/75 |
| 4,053,979 | 10/1977 | Tuthill et al. | 128/305 |
| 4,208,791 | 6/1980 | Van Cleve | 30/49 |
| 4,221,222 | 9/1980 | Detsch | 128/304 |
| 4,384,406 | 5/1983 | Tischlinger | 128/305 |
| 4,459,744 | 7/1984 | Esnard | 30/49 |

FOREIGN PATENT DOCUMENTS 430442 7/1926 Fed. Rep. of Germany .......... 30/53

Primary Examiner—Gene Mancene
Assistant Examiner—Cary E. Stone
Attorney, Agent, or Firm—Christel, Bean & Linihan

[57] ABSTRACT

A holder for a curette blade having two opposite sides, two opposite lateral edges and a cutting edge extending between the two edges utilizes two arcuate and opposing blade-clamping surfaces mounted for movement toward and away from one another and associated stop pins for abutting the opposite lateral edges of the blade when the blade is held between the blade-clamping surfaces. The blade-clamping surfaces are adapted to bend the blade into the shape of their arcs when the blade-clamping surfaces are moved from an opened condition to a closed condition so that the cutting edge of the blade is bent to an arcuate condition for a cutting or scraping operation. The holder further includes a member for releasably locking the blade-clamping surfaces in their closed condition about a blade.

20 Claims, 11 Drawing Figures

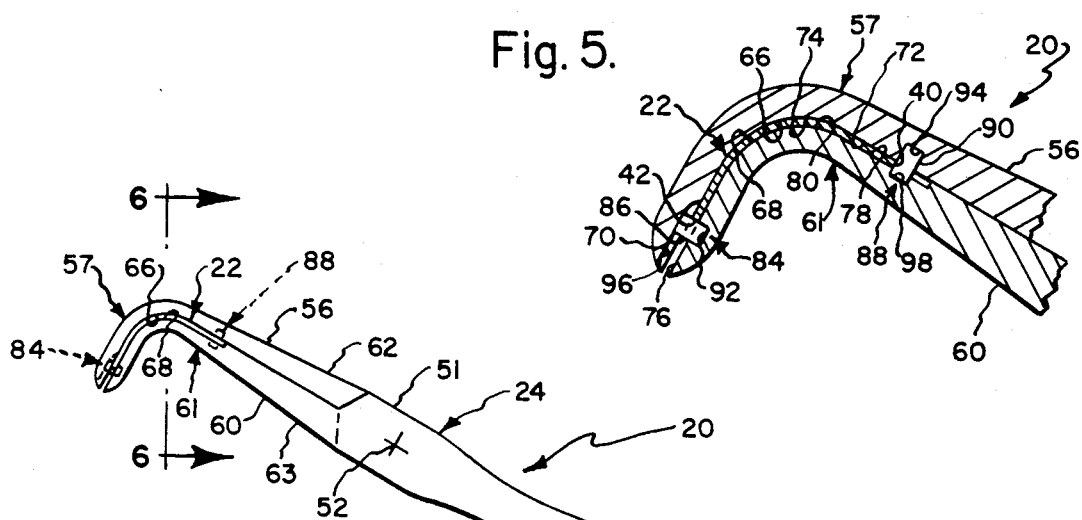
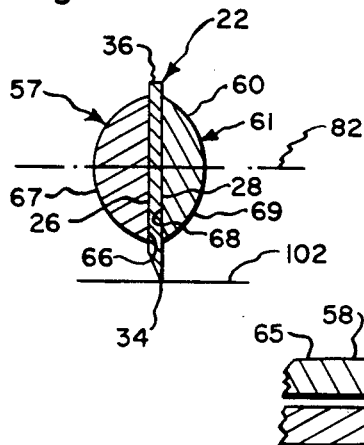
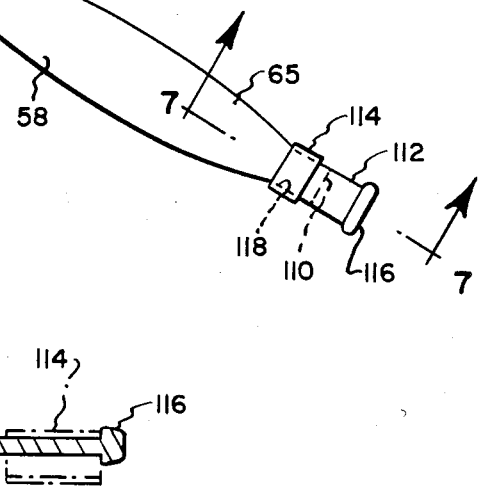
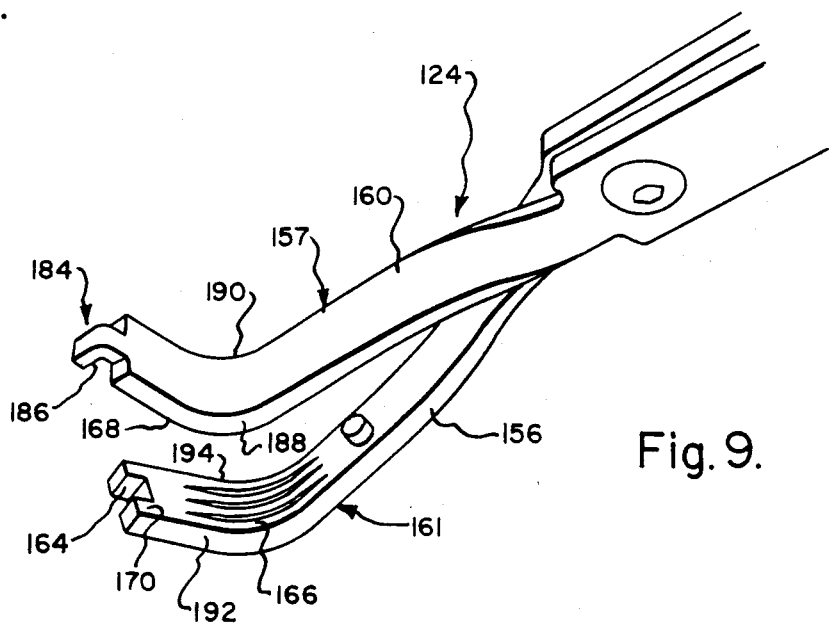

CURETTE BLADE HOLDER

BACKGROUND OF THE INVENTION

This invention relates, in general, to curettes for scraping and cutting of bodily tissue and relates, more particularly, to improved means for holding the working element of a curette during a scraping or cutting operation.

Curettes with which this invention is concerned are utilized in medical practice to scrape the surfaces of skin or body cavities in order to clean such surfaces, to remove skin lesions or foreign matter, or to obtain tissue or other materials for diagnostic purposes. Each of such curettes has a working element having a sharpened edge which, when moved in a scraping or cutting action across an area to be worked, removes the topmost layers of tissue. Of course, the extent of tissue removal by the working element is dependent upon the pressure applied to the area by the sharpened edge, the angle of the blade in relation to the tissue surface and the character of tissue involved. Commonly, the working element is of a loop or ring-type conformation and its sharpened edge is provided by a curved or circular working edge of the conformation.

Conventional curettes are limited in that any resharpening of the working element is difficult and time-consuming. Such difficulty is due, at least in part, to the fact that the working element of the curette is commonly constructed integrally with the handle of the device and the curved or circular working edge, because of its curvature, is difficult to align with a sharpening tool. Typically, a conventional curette must be sent to a professional for resharpening and because such action renders the curette unavailable for a time, the curette is likely to be used in a dulled condition throughout much of its life.

It is an object of the present invention to provide improved means for holding a working element, or blade, of a curette wherein the working element is easily removable for replacement or resharpening.

Another object of the present invention is to provide such means for holding the sharpened edge of a working element in an arcuate condition which facilitates a cutting or scraping operation.

Still another object of the present invention is to provide an improved curette having a deformable blade which is held in a deformed or arcuate condition for use and which can be easily removed and flatened for ease of sharpening or, alternatively, can be discarded and replaced with a new, sharp blade.

Yet still another object of the present invention is to provide such a curette having a blade which is well-suited for making small, closed-path incisions.

SUMMARY OF THE INVENTION

This invention resides in a holder for a curette blade of the type having two opposite sides, two opposite lateral edges and a cutting edge extending between the lateral edges.

The holder includes means defining two arcuate and opposing blade-clamping surfaces mounted for movement toward and away from one another. Each of the blade-clamping surfaces defines a first end portion adjacent one end of its arc, a second end portion adjacent the other end of its arc, and a central portion positioned between said first and second end portions. The blade-clamping surfaces are so arranged in relationship to one another that the first end portions oppose one another and the second end portions oppose one another. A first stop means is associated with a first end portion of one of the blade-clamping surfaces for abutting one lateral edge of a curette blade, and a second stop means is associated with the second end portion of the other blade-clamping surface for abutting the other lateral edge of the curette blade.

The holder further includes means for moving the blade-clamping surfaces toward and away from one another between an opened condition at which the curette blade can be operatively inserted therebetween so that each blade side generally faces a corresponding one of said blade-clamping surfaces, the lateral edges of the blade are positioned generally between the first and second stop means, and the cutting edge of the blade is positioned generally to one side of the blade-clamping surfaces and a closed condition at which the first and second stop means operatively abut the lateral edges of the blade and the blade-clamping surfaces pressingly engage the blade sides so that the cutting edge of the blade is tightly held in an arcuate condition for a cutting or scraping operation. The holder still further includes means for locking the blade-clamping surfaces in the closed condition.

BRIEF DESCRIPTION OF THE DRAWINGS

FIG. 4 is a view similar to FIG. 3 illustrating the blade-clamping surfaces when arranged in a closed condition.

FIG. 5 is a longitudinal cross-sectional view of a fragment of the FIG. 1 embodiment as shown in FIG. 4 and drawn to a slightly larger scale.

FIG. 6 is a cross-sectional view taken about on line 6—6 of FIG. 4.

FIG. 7 is a cross-sectional view taken about on line 7—7 of FIG. 4.

FIG. 9 is a fragmentary perspective view of an alternative embodiment of a holder in accordance with the present invention shown with its blade-clamping surfaces arranged in an opened condition.

DETAILED DESCRIPTION OF ILLUSTRATIVE EMBODIMENTS

Figure 1:
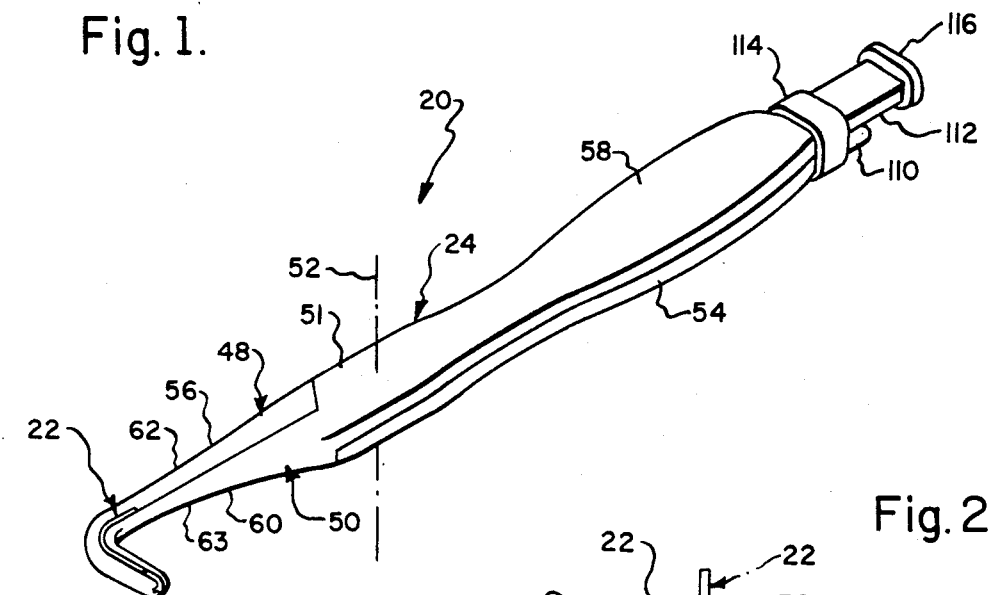
FIG. 1 is a perspective view of a curette in which one embodiment of a holder in accordance with the present invention is utilized.

Turning now to the drawings in greater detail and considering first FIG. 1, there is shown a curette, generally indicated 20, utilizing a blade 22 and holder 24 in accordance with the present invention. The holder 24 is adapted to firmly hold the blade 22 in an arcuate condition for a cutting or scraping operation while the holder 24 is, in turn, held by a hand of the user. Structural features of the holder 24, set forth in greater detail hereinafter, permit the blade 22 to be easily removed from the holder 24 for purposes of cleaning, sharpening or replacement.

Figure 2:
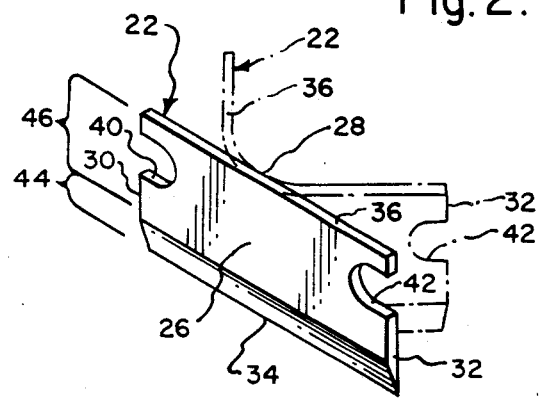
FIG. 2 is a perspective view of the blade held by the FIG. 1 embodiment.

The blade 22, best shown in FIG. 2, is constructed of a resiliently deformable metal, which, when in its undeformed or solid-line condition, is substantially planar. The blade 22 includes two opposite sides 26,28, two opposite lateral edges 30,32 a sharpened linear cutting edge 34, and a linear back edge 36 which is substantially parallel to the cutting edge 34. The sides 26,28 are relatively close together and the lateral edges 30,32 are generally arranged at right angles to the cutting edge 34 and back edge 36 so that the blade 22 is thin and rectangular in appearance.

Defined along each lateral edge 30 or 32 is a U-shaped notch 40 or 42 as shown in FIG. 2. Each notch 40 or 42 is positioned along the length of its corresponding lateral edge 30 or 32 so as to be positioned generally opposite the other notch 42 or 40. For a reason which will be hereinafter apparent, a cutting edge portion of the blade 22 which defines the cutting edge 34 is indicated 44 and the remaining, major portion of the blade 22 adjacent the cutting edge portion 44 is indicated 46.

Figure 3:
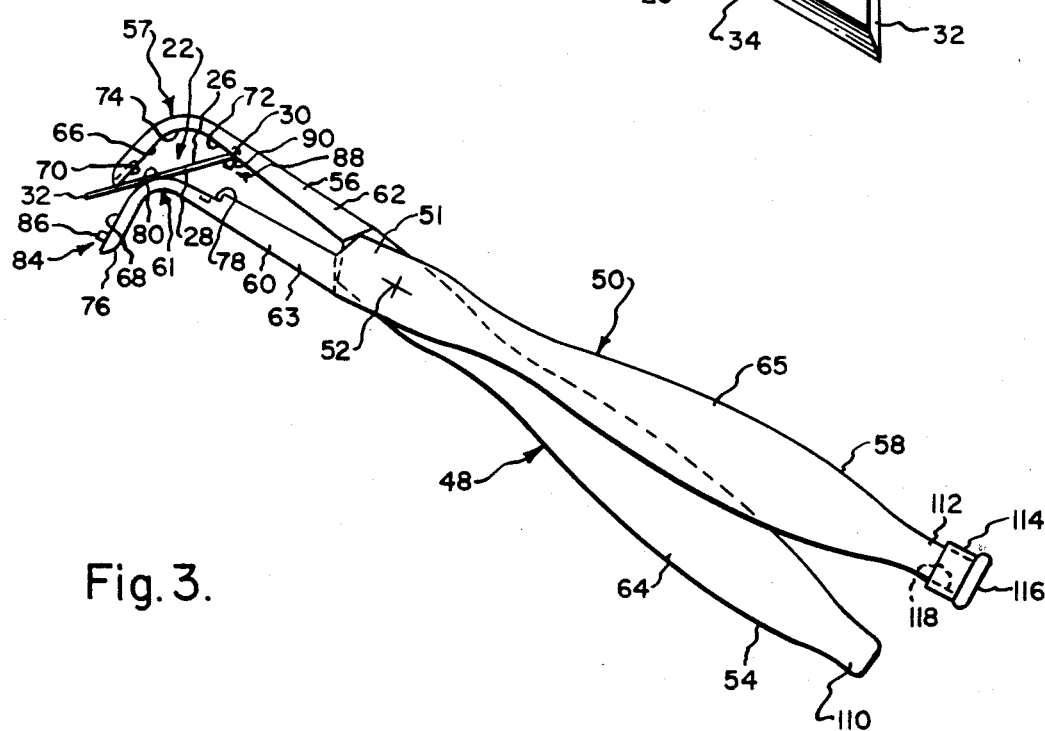
FIG. 3 is a plan view of the FIG. 1 embodiment with its blade-clamping surfaces shown arranged in an opened condition.

With reference to FIGS. 1,3 and 4, the holder 24 includes two pincerlike lever members 48,50 which are pivotally connected together in a joint arrangement 51 for pivotal movement relative to one another about a pivot axis indicated 52. The lever member 48 includes an elongated effort arm portion 54 and a response arm portion 56, and the lever member 50 includes an elongated effort arm portion 58 and a response arm portion 60. When the holder 24 is arranged in a closed condition as shown in FIGS. 1 and 4, the response arm portions 56 and 60 are arranged adjacent one another in a substantially side-by-side relationship and the effort arm portions 54 and 58 are closed together as shown in FIG. 4. When the holder 24 is arranged in an opened condition as shown in FIG. 3, the response arm portions 56 and 60 generally form an acute angle with one another and the effort arm portions 54 and 58 generally form an acute angle with one another. It will be understood that by pivotally moving the effort arm portions 54 and 58 relative to one another between opened and closed conditions, the response arm positions 56 and 60 move relative to one another between opened and closed conditions.

Each lever member 48 or 50 includes a relatively rigid shank 62 or 63 constructed, for example, of steel, and the effort arm portions 54 and 58 of the lever members 48 and 50, respectively, are so shaped as to provide a comfortable grip for a user when the lever members 48 and 50 are arranged in the closed condition of FIGS. 1 and 4. As shown in FIGS. 3 and 4, the effort arm protions 54 and 58 include enlarged regions 64 and 65, respectively.

With reference to FIG. 3-6 and in accordance with the present invention, the response arm portions 56,60 include jaws 57,61 which define arcuate and opposing blade-clamping surfaces 66 and 68, respectively. As best shown in FIG. 6, the body of each jaw 57 or 61 further defines an outer, rounded surface 67 or 69 which joins the blade-clamping surface 66 or 68 at the edges, or the upper and lower edges as viewed in FIG. 6, of the surface 66 or 68. As best shown in FIG. 3, the blade-clamping surface 66 defines a first end portion 70 adjacent one end of its arc, a second end portion 72 adjacent the other end of its arc, and a central portion 74 positioned between the two end portions 70 and 72. The blade-clamping surface 68 defines a first end portion 76 adjacent one end of its arc, a second end portion 78 adjacent the other end of its arc and a central portion 80 positioned between the two end portions 76 and 78. Each surface 66 and 68 is generally smooth and continuous between the ends of its arc and is relatively narrow in shape as measured between its edges, or upper and lower edges as viewed in FIG. 6.

The L-shaped arc of each blade-clamping surface 66 or 68 is so arranged in relationship to the lever members 48 and 50 that one leg of its L is directed along a path which is generally parallel to the longitudinal axis of its corresponding effort arm portion 54 or 58 and the other leg of its L is directed along a path which is generally perpendicular to the longitudinal axis of its corresponding effort arm portion 54 or 58. More specifically, the second end portion 72 of blade-clamping surface 66 is directed generally along a path which is oriented parallel to the longitudinal axis of effort arm portion 54, the first end portion 70 of blade-clamping surface 66 is directed generally along a path which is oriented perpendicular to the longitudinal axis of effort arm portion 54, the second end portion 78 of blade-clamping surface 68 is directed generally along a path which is oriented parallel to the longitudinal axis of effort arm portion 58, and the first end portion 76 of blade-clamping surface 68 is directed generally along a path which is oriented perpendicular to the longitudinal axis of effort arm portion 58. Furthermore, the blade-clamping surfaces 66,68 are so arranged in relationship to the pivot axis 52 that movement of the surfaces 66 and 68 toward and away from one another confines the relative movement of the L-shaped arcs of the surfaces 66 and 68 to a plane which is generally perpendicular to the pivot axis 52.

There is shown in FIG. 6 a longitudinal midplane of the blade-clamping surfaces 66,68 indicated 82. It will be understood that the blade-clamping surfaces 66,68 are so arranged in relationship to the midplane 82 that imaginary lines can be traced across each surface 66,68 from one edge to the other, or from the upper edge to the lower edge as viewed in FIG. 6, which are generally perpendicular to the midplane 82. As viewed in a direction perpendicular to the midplane 82, or in the plan views of FIGS. 3-5 each arc of the blade-clamping surfaces 66,68 is generally L-shaped in appearance with a rounded central, or knee, portion 74 or 80. The blade-clamping surface 66 faces radially inwardly of its corresponding arc so as to be considered generally concave in shape, and the blade-clamping surface 68 faces radially outwardly of its corresponding arc so as to be considered generally convex in shape.

With reference still to FIGS. 3-5 and in accordance with the present invention, stop means are associated with the blade-clamping surfaces 66,68 for abutting the opposite lateral edges 30,32 of the blade 22 when the blade 22 is operatively held therebetween. More specifically, a first stop means 84 in the form of a small cylindrical pin 86 is fixedly connected to the response arm portion 60 so as to provide the blade-clamping surface 68 with a protrusion extending generally perpendicularly from the surface of the first end portion 76. A second stop means 88 in the form of a small cylindrical pin 90 is fixedly connected to the response arm portion 56 so as to provide the blade-clamping surface 66 with a protrusion extending generally perpendicularly from the surface of the second end portion 72. The longitudinal centerline of each pin 86 or 90 is contained within the midplane 82 (FIG. 6), and each pin 86 or 90 is of such size to be closely received by a corresponding one of the U-shaped notches 40,42 in the blade edges 30,32 when a blade edge 30 or 32 is placed thereagainst.

With reference to FIG. 5, the first end portion 76 of the blade-clamping surface 68 defines a substantially circular recess 92 within which one end of the pin 86 is fixedly received, and the second end portion 72 of the blade-clamping surface 66 defines a substantially circular recess 94 within which one end of the pin 90 is fixedly received. Each pin 86 or 90 is held within its corresponding recess 92 or 94 by means of a press fit or weld. The first end portion 70 of the blade-clamping surface 66 defines a slot or groove 96 for loosely accepting the free, unattached end of the pin 86 when the surfaces 66 and 68 are moved from the opened condition of FIG. 3 to the closed condition of FIGS. 4 and 5, and the second end portion 78 of the blade-clamping surface 68 defines a cylindrical recess 98 for loosely accepting the free, unattached end of the pin 90 when the surfaces 66 and 68 are moved from the FIG. 3 opened condition to the closed condition of FIGS. 4 and 5.

In order to operatively position the blade 22 between the blade-clamping surfaces 66,68, the effort arm portions 54,58 of the lever members 48,50 are pivotally moved relative to one another to position the response arm portions 56,60 in the FIG. 3 opened condition. The major section 46 of the blade 22 is then inserted by hand between the blade-clamping surfaces 66,68 so that each blade side 26 or 28 generally faces a corresponding one of the blade-clamping surfaces 66 or 68 and the blade lateral edges 30 and 32 are positioned generally between the stop means 88 and 84. As the blade 22 is shown operatively inserted between the surfaces 66 and 68 in FIG. 3, the lateral edge 30 engages the second end portion 72 of the blade-clamping surface 66 so that the notch 40 accepts the pin 90 and the lateral edge 32 extends beyond the first end portion 70 of the surface 66.

The effort arm portions 54 and 58 are subsequently moved from the opened condition of FIG. 3 to the closed condition of FIG. 4 to move the response arm portions 56 and 60 from the FIG. 3 opened condition to the FIG. 4 closed condition. When the response arm portions 56 and 60 move toward one another to the FIG. 4 closed condition, the blade-clamping surface 68 makes initial contact with the blade 22 when the central portion 80 engages the blade side 28. The blade 22 is thereafter frictionally held or supported between the surfaces 66 and 68 so that the blade 22 can be turned loose by the hand used to initially insert the blade 22 between the surfaces 66 and 68. Further movement of the response arm portions 56 and 60 toward one another moves the pin 86 into the blade notch 42 defined along the blade edge 32 and forces the surfaces 66 and 68 to squeeze the blade 22 into an arcuate condition conforming to the arc of the surfaces 66 and 68. The blade 22 is thereby captured between the pins 86 and 90 and each of the blade sides 26 and 28 engages a corresponding one of the surfaces 66,68 along a continuous path traced between the first and second end portions of the corresponding surface 66 or 68.

The pins 86 and 90 abut the blade lateral edges 32 and 30 at relative positions of the response arm portions 56 and 60 which immediately precede the FIG. 4 closed condition so that subsequent movement of the response arm portions 56 and 60 toward one another forces the pins 86 and 90 to compress the blade 22 endwise between the lateral edges 32 and 30. It is believed that such compression effectively contributes to the bending of the blade 22 from its undeformed condition, shown in solid lines in FIG. 2, to its operative, deformed condition, shown in phantom lines in FIG. 2, and that the rigidity with which the blade 22 is held between the blade-clamping surfaces 66 and 68 when in the FIG. 4 closed condition is thereby enhanced. The pin 86 and the corresponding groove 96 of the blade-clamping surface 66 provide a further advantage in that once the pin 86 is received in the groove 96, the first end portions 70 and 76 of the blade-clamping surfaces 66 and 68 are prevented from sliding relative to one another into and out of the plane of movement about the pivot axis 52. Thus, the cooperation of the pin 86 and groove 96 contribute to the rigidity with which the blade-clamping surfaces 66 and 68 are held in the closed condition.

When the blade 22 is operatively held between the blade clamping surfaces 66 and 68 in the manner shown in FIG. 4, the blade 22 is prevented from moving relative to the blade clamping surfaces 66 and 68 by means of the pins 86 and 90 and the frictional gripping engagement between each of the blade clamping surfaces 66 or 68 and a corresponding one of the blade sides 26 or 28. Furthermore, and as shown in FIG. 6, the cutting edge section 44 of the blade 22 protrudes to one side of the response arm portions 56 and 60 to thereby expose the cutting edge 34 for use. When operatively held in its arcuate condition for cutting and with reference to FIG. 6, the cutting edge 34 lies within a plane, indicated 102, which is generally parallel to the midplane 82 of the response arms portions 56 and 60. It will be understood that imaginary line segments drawn across the blade sides 26,28 before deformation of the blade 22 and oriented at right angles to the cutting edge 34 are linear, and that such imaginary line segments remain linear after deformation of the blade 22 and are oriented generally perpendicular to the plane 102 of the cutting edge 34.

The aforedescribed curvature of the blade 22 and its relationship to the lever members 48 and 50 provides an advantage when the blade 22 is used to remove a specimen in depth. More specifically, by grasping the holder 24 as one would grasp a pencil and orienting the sides of the blade 22 at an appropriate angle in relation to the surface of tissue adjacent the specimen to be removed, the blade 22 can be easily moved in a gouging or scooping action to undermine and thereby separate the specimen from the remainder of the tissue. In contrast, a flat-bladed surgical scalpel, commonly utilized for removing tissue specimens, is adapted to be moved in a cutting or slicing action rather than a gouging or scooping action, and is therefore more difficult to manipulate than is the holder 24 when removing a specimen in depth.

A further advantage provided by the holder 24 relates to the ease with which the blade 22 can be removed for purposes of cleaning, resharpening or replacement. More specifically, the blade 22 is simply released by the blade-clamping surfaces 66 and 68 by moving the effort arm portions 54 and 58 relative to one another so that the response arm portions 56 and 60 move from the FIG. 4 closed condition to the FIG. 3 opened condition. Once the grip of the blade-clamping surfaces 66,68 is released, the blade 22 can be removed by hand from the space between the two surfaces 66 and 68. Because the blade 22 is resilient, it can be easily flattened to a planar condition for ease of sharpening. Alternatively, the blade 22 can be discarded and replaced with a sharpened blade similar in construction to that of blade 22.

Figure 8:
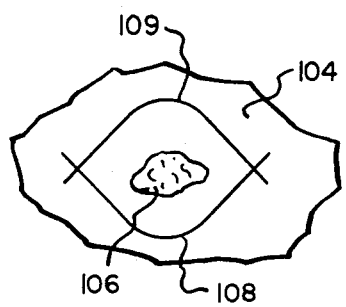
FIG. 8 is a fragmentary plan view of a region of tissue illustrating the cuts of a small, closed-path incision made with the holder and blade of FIG. 1.

A still further advantage provided by the holder 24 relates to the making of small, closed-path incisions. For example, there is shown in FIG. 8 a region of tissue 104 having a blemished area 106 which is desired to be removed. By appropriately manipulating the holder 24 and pressing the blade edge 34 against the tissue 104 to effect two intersecting arcuate cuts 108,109 as shown, the blemished area 106 can be easily and quickly separated from the remainder of the tissue region 104. In contrast, a flat-bladed scalpel commonly used to make small, closed path incisions, is much more dififcult to manipulate and is thus much slower to use than is the holder 24 to effect such incisions.

Inasmuch as the holder 24 and blade 22 have been described for use in medical cutting or scraping applications, it will be understood that the holder 24 and blade 22 are also well-suited for use in other cutting applications such as the tooling of leather and the carving and whittling of wood. In such non-medically related applications, the curved edge of the blade 22 can be used to cut or gouge areas of a workpiece which may otherwise be hard to work with flat-bladed knife.

Although the positioning of the blade 22 between the jaws 57 and 61 of the holder 24 so that the blade cutting edge 34 protrudes to one side of the jaws 57 and 61 may better accommodate a right-handed user of the holder 24 than a left-handed user, it will be understood that the blade 22 can be simply removed from the holder 24, as shown, and repositioned between jaws 57 and 61 in an inverted condition so that the cutting edge 34 protrudes to the other side of the jaws 57 and 61. Thus, it will be understood that the holder 24 is neither right nor left "handed" and can thus be suitably utilized by right and left handed users.

With reference to FIGS. 3, 4 and 7 and in accordance with the present invention, the holder 24 includes means for releasably locking the blade-clamping surfaces 66,68 in the FIG. 4 closed condition. In the holder 24, the means for releasably locking are provided by the free end portions, indicated 110 and 112 of the effort arm portions 54 and 58, respectively, and a ring 114. As best shown in FIG. 7, each free end portion 110 or 112 is an integral extension of the shank 62 or 63 of its corresponding lever member 54 or 58, and the free end portion 112 extends from the pivot axis 52 of the joint 51 for a distance which is slightly greater than the distance from which the free end portion 110 extends from the pivot axis 52 and includes an end abutment section 116. Referring again to FIG. 3, the ring 114 defines a central through opening 118 through which free end portion 112 is received and is of such size that the enlarged region 64 of the effort arm portion 58 limits the sliding movement of the ring 114 in one direction therealong and the abutment end section 116 limits sliding movement of the ring 114 in the other direction therealong. When the ring 114 is positioned in abutting relationship with the abutment end section 116, the ring 114 does not interfere with the relative movement of the effort arm portions 54 and 58.

Referring to FIG. 7, the through-opening 118 of the ring 114 is of such size to snugly receive, in addition the the free end portion 112, the free end portion 110 when the effort arm portions 54 and 58 are positioned in the FIG. 4 closed condition. To position the ring 114 about the free end portions 110 and 112, the effort arm portions 54 and 58 are simply moved to the FIG. 4 closed condition and the ring 114 is slidably placed over both of the free end portions 110 and 112. By pressing the ring 114 over the free end portions 110 and 112 when positioned in the FIG. 4 closed condition, the free end portions 110 and 112 frictionally grips the ring 114 and thereby releasably hold the ring 114 in place. Inasmuch as the resiliency of the blade 22 effectively biases the blade-clamping surfaces 66 and 68 and thus the effort arm portions 54 and 58 apart, such resiliency also enhances the aforedescribed frictional grip between the free end portions 110 and 112 and the ring 114.

It follows from the above that when the ring 114 is placed about the free end portions 110 and 112, the effort arm portions 54 and 58, and subsequently the blade-clamping surfaces 66 and 68, are releasably locked in the FIG. 4 closed condition. To unlock the blade-clamping surfaces 66,68 from the locked condition as shown in FIG. 4, the ring 114 is simply slidably moved relative to the free end portion 112 from its FIG. 7 solid line position to the FIG. 7 position indicated in phantom. With the ring 114 positioned in abutment with the abutment end section 116, the effort arm portions 54,58, and thus the blade-clamping surfaces 56,58 are permitted to move relative to one another.

It will be understood that numerous modifications and substitutions may be made to the aforedescribed embodiment without departing from the spirit of the invention. For example, although the response arm portions 56 and 60 of the holder 24 have been shown and described as being substantially rounded in cross section, there is shown in FIG. 9 an embodiment of a holder, generally indicated 124, having response arm portions 156,160 defining jaws 157,161 which are substantially rectangular in cross section. For purposes of making small, closed-path incisions described above, the rectangular cross-sectional shape of the jaws 157,161 may be preferred over the rounded cross-sectional shape of the jaws 57,61 of holder 124 because the flat edges, indicated 188,190,192,194 serve as suitable stops to thereby limit the movement of the blade into the tissue surface.

Futhermore, although the blade-clamping surfaces 66 and 68 have been shown and described as being generally smooth, the blade-clamping surfaces can be rough in accordance with the broader aspects of this invention. For example, there is shown in the holder 124 of FIG. 9, blade-clamping surfaces 166 and 168 defining a ribbed pattern therealong. Such a ribbed, or rough, pattern is believed to enhance the frictional gripping engagement between the blade-clamping surfaces 166 and 168 and a blade held therebetween.

Still further, although the stop means of the holder 24 of FIGS. 1-7 have been shown and described as including small cylindrical pins 86 and 90, there is shown in the FIG. 9 holder 124 stop means 184 in the form of a narrow stem 186. The stem 186 is an integral extension of the response arm portion 160 and is bent in such a manner as to extend generally radially outwardly of the arc of curvature of the blade-clamping surface, indicated 168, of the response arm portion 160. Defined in the end portion, indicated 170, of the other blade-clamping surface, indicated 166, which generally opposes the stem 186 is a notch 164 adapted to accept the stem 186 when the response arm portions 156 and 160 are moved into a closed condition.

Figure 10:
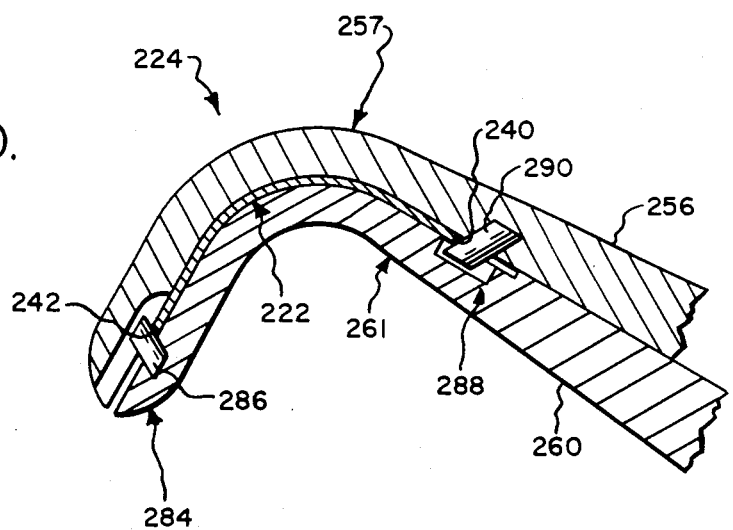
FIG. 10 is a view similar to FIG. 5 illustrating the jaws of another embodiment of a holder in accordance with the present invention.
Figure 11:
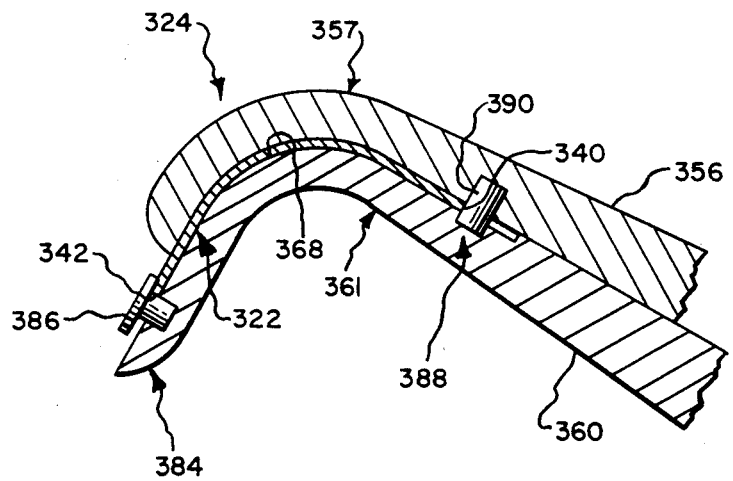
FIG. 11 is a view similar to FIG. 5 illustrating the jaws of still another embodiment of a holder in accordance with the present invention.

Yet still further and with reference to FIGS. 10 and 11, there are shown alternative embodiments of holders, generally indicated 224 and 324 respectively, illustrating further forms which the holder stop means can take. Holder 224 of FIG. 10 includes response arm portions 256,260 having jaws 257,261 to which are attached stop means 288,284 in the form of truncated cylindrical pins 290,286. As shown in FIG. 10, each pin 290 or 286 is retainably received by an appropriately-angled recess in its corresponding response arm portion 256 or 260 so that its cylindrical surface extends angularly from the end portion of the jaw 257 or 261 toward the central portion of the jaw to which it is connected. By angling the free end of the pins 286 and 290 as aforesaid, the pins 286 and 290 effectively prevent the lateral edges of blade 222 from moving or springing away from the jaw 257 once the pins 286 and 290 are moved in abutting relationship with the blade positioned between the jaws 257,261, and effectively holds each blade lateral edge against a corresponding jaws end portion to which the pin 286 or 290 is connected. Furthermore, because the pin 286 holds one lateral edge of the blade 222 against the free end of the jaw 261, the blade 222 can be operatively inserted between the jaws 257,261, when opened, by initially positioning the notch 242 of one blade lateral edge against the pin 286 and orienting the longitudinal axis of the blade 222 generally between the jaws 257,261. Subsequent movement of the jaws 257,261 toward one another forces the blade 222 into an arcuate condition while the other lateral edge of the blade 222 is guided along the surface of the jaw 257 until its notch 240 abuts the pin 290.

As shown in FIG. 11, holder 324 includes response arm portions 356,360 having jaws 357,361 to which are attached stop means 384,388. Stop means 388 is in the form of a cylindrical pin 390 fixedly attached to the jaw 357 in the same manner as pin 90 of the holder 24 of FIGS. 1-7 is attached to the holder jaw 57. Stop means 384 is in the form of a headed pin 386 fixedly attached to the free end portion of the jaw 361. The shank of the headed pin 386 is retainably received within a recess in the free end portion of the jaw 361, and the head of the pin 386 is spaced from the blade-clamping surface, indicated 368, of the jaw 361. The shank of the pin 386 thus provides suitable means for preventing endwise movement in one direction of a blade 322 positioned between the jaws 357,361, and the head of the pin 386 thus provides a means for preventing the blade 322 from moving or springing away from the jaw 357 once the pins 386,390 are moved in abutting relationship with the blade notches 342,340, respectively. Furthermore, the head of the pin 386 effectively holds one lateral edge of the blade against the free end of the jaw 361 so that the free end of the jaw 357 can be truncated and is shown in FIG. 11 as such.

Moreover, although the blade 22 has been shown and described as generally rectangular so as to provide the cutting edge 34 with square corners, the corners of the blade cutting edge can take any of several shapes such as a rounded or slanted shape.

Accordingly, the aforedescribed embodiment of the curette 20 of FIGS. 1-7 is intended for purposes of illustration and not as limitation.

I claim:

1. A holder for a curette blade of the type having two opposite sides, two opposite lateral edges and a cutting edge extending between the lateral edges, said holder comprising:

means defining two arcuate and opposing blade-clamping surfaces mounted for movement toward and away from one another, each of said blade-clamping surfaces having two end portions adjacent the ends of its arc and generally opposing the other blade-clamping surface for a substantial distance along its length;

a first stop means associated with one end portion of one of said blade-clamping surfaces for abutting one lateral edge of a curette blade;

a second stop means associated with one end portion of the other of said blade-clamping surfaces for abutting the lateral edge of the curette blade opposite said one lateral edge;

means for moving said blade-clamping surface toward and away from one another and between an opened condition at which the blade can be operatively inserted therebetween so that each of the blade sides generally faces a corresponding one of said blade-clamping surfaces, the lateral edges of the blade are positioned generally between said first and second stop means and the cutting edge of the blade is positioned generally to one side of said blade-clamping surfaces and a closed condition at which each of said first and second stop means operatively abut a corresponding one of the lateral edges of the blade and each of said blade-clamping surfaces pressingly engage a corresponding one of said blade sides along a path extending between said blade lateral edges so that the cutting blade is tightly held in an arcuate condition for a cutting or scraping operation, said means for moving including two lever members pivotally connected together for pincerlike movement about a pivot axis, each lever member including an effort arm portion and a response arm portion and each of said response arm portions being operatively associated with a corresponding one of said blade-clamping surfaces so that movement of said effort arm portions toward and away from one another moves said blade-clamping surfaces toward and away from one another; and means for locking said blade-clamping surfaces in said closed condition.

2. A holder as defined in claim 1 wherein each of said stop means includes detent means defining a protrusion extending generally away from the blade-clamping surface with which it is associated, each of said protrusions defining an abutment surface for abutting a corresponding one of the lateral edges of the blade and thereby preventing relative movement between said protrusions and the lateral edges of the blade when said blade-clamping surfaces are positioned in said closed condition, each of said opposing blade-clamping surfaces adapted to accommodate a corresponding protrusion when said blade-clamping surfaces are moved from said opened condition to said closed condition.

3. A holder as defined in claim 2 wherein said abutment surfaces of said protrusions are so arranged along the length of said blade-clamping surfaces that the lateral edges of the blade are engaged by said abutment surfaces through relative positions of said blade-clamping surfaces immediately preceding the relative movement of said blade-clamping surfaces into said closed condition so that said protrusions effectively compress said blade edgewise through said relative positions and facilitate any bending of the blade to an arcuate condition.

4. A holder as defined in claim 3 wherein each of said protrusions is provided by a small pin fixedly attached to its corresponding end portion.

5. A holder as defined in claim 1 wherein each of said blade-clamping surfaces has a first end portion, a second end portion and a central portion positioned between said first and second end portions, said first end portions of said blade-clamping surfaces are arranged so as to oppose one another and said second end portions are arranged so as to oppose one another, said one end portion of one blade-clamping surface is provided by said first end portion of the one blade-clamping surface and said one end portion of the other blade-clamping surface is provided by said second end portion of the other blade-clamping surface.

6. The holder as defined in claim 1 wherein each of said blade-clamping surfaces is somewhat L-shaped along the length of its arc and is so arranged in relationship to said pivot axis that the legs of its L are contained generally in a plane oriented perpendicular to said pivot axis and one leg of the L is generally directed toward said pivot axis.

7. A holder as defined in claim 1 wherein each arc of said blade-clamping surfaces is generally L-shaped, each of said effort arm portions is elongated and adapted to be manually held during a cutting or scraping operation, and one leg of each L of said blade-clamping surfaces is generally aligned with the longitudinal axis of its corresponding effort arm portion.

8. A holder as defined in claim 7 wherein the other leg of each L of said blade-clamping surfaces is arranged generally perpendicular to the longitudinal axis of its corresponding effort arm portion.

9. A holder as defined in claim 8 wherein said other leg of each L is oriented generally perpendicular to said pivot axis.

10. A holder as defined in claim 1 wherein said means for locking includes means for releasably locking the positional relationship of said effort arm portions relative to one another so that said blade-clamping surfaces are locked in said closed condition.

11. A holder as defined in claim 10 wherein each of said effort arm portions has a free end section which is positioned adjacent the free end section of the other of said effort arm portions when said blade-clamping surfaces are arranged in said closed condition and said means for releasably locking includes a ring-like member having an opening for receiving both of said free end sections when said free end sections are positioned adjacent one another to thereby bind said free end sections together.

12. A curette comprising:
 a blade having two opposite sides, two opposite lateral edges, and a cutting edge extending between said lateral edges and having a major section and a cutting edge section positioned adjacent said major section, said cutting edge being defined along the cutting edge section; and
 a blade holder including
 (a) means defining two arcuate blade-clamping surfaces mounted for movement toward and away from on another, each of said blade-clamping surfaces having two end portions adjacent the ends of its arc and generally opposing the other blade-clamping surface for a substantial distance along its length,
 (b) a first stop means associated with one end portion of one of said blade-clamping surfaces for abutting one lateral edge of said blade,
 (c) a second stop means associated with one end portion of the other of said blade-clamping surfaces for abutting the lateral edge of said blade opposite said one lateral edge,
 (d) means for moving said blade-clamping surfaces toward and away from one another between an opened condition at which said major section of said blade can be inserted therebetween so that each of said blade sides generally faces a corresponding one of said blade-clamping surfaces and said lateral edges are positioned generally between said first and second stop means and a closed condition at which said first and second stop means are moved into abutting relationship with said lateral edges of said blade and said blade-clamping surfaces pressingly engage said blade sides so that the shape of said blade is conformed to the shape of the arc of each of said blade-clamping surfaces and said blade is tightly held between said blade-clamping surfaces for a cutting or scraping operation, said means for moving including two lever members pivotally connected together for pincerlike movement about a pivot axis, each lever member including an effort arm portion and a response arm portion and each of said blade-clamping surfaces being defined by a corresponding one of said response arm portions so that movement of said effort arm portions toward and away from one another moves said blade-clamping surfaces toward and away from one another; and
 (e) means for locking said blade-clamping surfaces in said closed condition.

13. A curette as defined in claim 12 wherein said blade is deformable and substantially planar when in an undeformed condition, said cutting edge of said blade is substantially linear when said blade is in said undeformed condition and said blade-clamping surfaces are so arranged in relationship to one another than when moved from said opened condition to said closed condition, said blade-clamping surfaces bend said blade to a deformed condition so that imaginary line segments drawn across said sides of said blade and oriented at right angles to said cutting edge before deformation of said blade remain linear after deformation of said blade.

14. A curette as defined in claim 12 wherein each of said stop means includes detent means defining a protrusion extending generally away from the blade-clamping surface with which it is associated, each of said protrusions defining an abutment surface for abutting a corresponding one of the lateral edges of said blade when said blade-clamping surfaces are positioned in said closed condition, each of said opposing blade-clamping surfaces adapted to accommodate a corresponding protrusion when said blade-clamping surfaces are moved from said opened condition to said closed condition.

15. A curette as defined in claim 14 wherein each of said lateral edges of said blade defines a notch adapted to nestingly accept a corresponding one of said protrusions when said blade-clamping surfaces are positioned in said closed condition to thereby enhance the rigidity of said blade when held by said holder.

16. A curette as defined in claim 12 wherein each of said blade-clamping surfaces has a first end portion, a second end portion and a central portion positioned between said first and second end portions, said first end portions of said blade-clamping surfaces are arranged so as to oppose one another and said second end portions are arranged so as to oppose one another, said one end portion of one blade-clamping surface is provided by said first end portion of the one blade-clamping surface and said one end portion of the other blade-clamping surface is provided by said second end portion of the other blade-clamping surface.

17. A curette defined in claim 12 wherein said means for moving are adapted to move said blade-clamping surfaces relative to one another about a pivot axis and the arc of each of said blade-clamping surfaces is substantially contained in one plane oriented generally perpendicular to said pivot axis so that movement of said blade-clamping surfaces toward and away from one another confines the relative movement of said blade-clamping surfaces to said one plane.

18. A curette as defined in claim 12 wherein each of said blade-clamping surfaces is generally L-shaped along the length of its arc and is so arranged in relationship to said pivot axis that the legs of its L are contained generally in a plane oriented perpendicular to said pivot axis and one leg of the L is generally directed toward said pivot axis.

19. A curette as defined in claim 12 wherein said means for locking includes means for releasably locking the positional relationship of said effort arm portions relative to one another so that said blade-clamping surfaces are releasably locked in said closed condition.

20. A curette as defined in claim 19 wherein each of said effort arm portions has a free end section which is positioned adjacent the free end section of the other of said effort arm portions when said blade-clamping surfaces are arranged in said closed condition and said means for releasably locking includes a ring-like member having an opening for receiving both of said free end sections when said free end sections are positioned adjacent one another to thereby bind said free end sections together.

* * * * *